(12) United States Patent
Santala et al.

(10) Patent No.: US 10,405,765 B2
(45) Date of Patent: Sep. 10, 2019

(54) MODULAR ELECTROCARDIOGRAM DEVICE WITH HIGH QUALITY DIFFERENTIAL LIMB-LEADS AND MODULARLY EXPANDABLE CHEST-LEADS

(71) Applicant: General Electric Company, Schenectady, NY (US)

(72) Inventors: Robert Filip Arnold Santala, Helsinki (FI); Ville Petteri Vartiovaara, Tuusula (FI); Juha Petri Virtanen, Helsinki (FI)

(73) Assignee: General Electric Company, Schenectady, NY (US)

( * ) Notice: Subject to any disclaimer, the term of this patent is extended or adjusted under 35 U.S.C. 154(b) by 379 days.

(21) Appl. No.: 15/059,922

(22) Filed: Mar. 3, 2016

(65) Prior Publication Data

US 2017/0251939 A1 Sep. 7, 2017

(51) Int. Cl.
| | | |
|---|---|---|
| *A61B 5/04* | (2006.01) | |
| *A61B 5/0402* | (2006.01) | |
| *A61B 5/0408* | (2006.01) | |
| *A61B 5/0428* | (2006.01) | |
| *A61B 5/00* | (2006.01) | |

(52) U.S. Cl.
CPC .......... *A61B 5/0402* (2013.01); *A61B 5/0006* (2013.01); *A61B 5/0408* (2013.01); *A61B 5/0428* (2013.01); *A61B 5/04282* (2013.01); *A61B 2560/0443* (2013.01)

(58) Field of Classification Search
CPC .......................... A61B 5/0408; A61B 5/04012
See application file for complete search history.

(56) References Cited

U.S. PATENT DOCUMENTS

| 5,307,817 A * | 5/1994 | Guggenbuhl | ........ A61B 5/0006 |
| | | | 128/908 |
| 7,881,778 B2 | 2/2011 | Rantala | |
| 2001/0027270 A1 * | 10/2001 | Stratbucker | ........ A61B 5/04085 |
| | | | 600/382 |
| 2002/0138011 A1 | 9/2002 | Rantala | |
| 2004/0210150 A1 * | 10/2004 | Virtanen | .............. A61B 5/0402 |
| | | | 600/509 |

OTHER PUBLICATIONS

International Search Report and Written Opinion for International Application No. PCT/US2017/017611, dated Apr. 18, 2017. 10 pages.

* cited by examiner

*Primary Examiner* — Michael J D Abreu
(74) *Attorney, Agent, or Firm* — Andrus Intellectual Property Law, LLP

(57) ABSTRACT

A data acquisition system for use with expandable ECG electrode systems. The data acquisition system includes a main unit and one or more expansion units for increasing the number of ECG leads applied to a patient for enhanced monitoring capabilities. Multiple embodiments are illustrated for providing a common mode signal between the main electrode unit and expansion units without requiring the physical transmission of voltage potential between the main unit and the expansion unit. In one embodiment, the main unit and the expansion unit share a common ground reference potential. In a second embodiment, an optical signal is transmitted between the main unit and the extension unit to relay the common mode information while in a third embodiment, common electrode potentials are provided to both the main unit and the extension unit for constructing their own common reference signal.

16 Claims, 6 Drawing Sheets

MODULAR ELECTROCARDIOGRAM DEVICE WITH HIGH QUALITY DIFFERENTIAL LIMB-LEADS AND MODULARLY EXPANDABLE CHEST-LEADS

BACKGROUND

The present disclosure generally relates to a wireless ECG device. More specifically, the present disclosure relates to a solution to modularly expand a wireless ECG device.

Electrocardiography (ECG) measures the electrical activity of the heart. It depicts the rate and the regularity of heartbeat as well as the presence of cardiac diseases or damage, arrhythmias etc. The ECG is one of the most important non-invasive diagnostic tools available to cardiologists. An ECG is measured by placing electrodes on the chest and limbs of the patient and measuring the bioelectrical potentials produced by the heart. Electrodes attached to the patient are connected by leads to an ECG monitor or communicate wirelessly to the ECG monitor for further signal processing.

Standard methods for obtaining an ECG from a subject are 3-lead, 5-lead, 12-lead or a 15-lead ECG. 3-lead and 5-lead ECGs are commonly used for routine ECG monitoring at hospitals. The 12-lead ECG monitoring provides much more information e.g. about possible cardiac ischemia, than is obtainable from the 3- or 5-lead ECG. Therefore, the 12-lead ECG is the most common of these methods and thus often referred to as the "standard 12-lead ECG". The 5-lead measurement provides seven signals: the limb leads I, II, III, aVR, aVL, aVF and one precordial lead e.g. V5. This measurement can be done by placing one electrode on each of the patient's four limbs at the wrists and ankles and one precordial electrode on the patient's chest. The limb electrodes are referred to as left arm (LA), right arm (RA), left leg (LL), and right leg (RL). For a standard 12-lead ECG, ten electrodes are attached to a patient's body in a manner described in FIG. 1. As shown in FIG. 1, six electrodes are attached in standard positions on the chest around the heart. The standard 12-lead ECG thus provides information from the frontal plane from limb leads I, II, III, aVR, aVL and aVF and from the horizontal plane from precordial leads V1, V2, V3, V4, V5 and V6. As is commonly known in the art, the ten electrodes are connected via lead wires and resistor networks to amplifiers to record twelve separate ECG channels or leads.

The frontal leads are obtained with various permutations of the LA, RA, and LL electrodes, with the RL electrode serving as an electrical ground. The frontal leads are comprised of the potential between two of the limb electrodes: lead I corresponds to the potential between LA and RA, lead II corresponds to the potential between LL and RA, and lead III corresponds to the potential between LL and LA. Leads aVR, aVL, and aVF, referred to as the augmented leads, are comprised of the potential between one electrode and a reference input, the reference input being the average of two electrodes. For example, lead aVF is the signal between LL and a reference input, where the reference input is the average of the potentials at electrodes RA and LA.

The horizontal leads V1-V6 are obtained with various permutations of the six electrodes attached to the patient's chest, in addition to three of the four limb electrodes. Each of the six horizontal leads is comprised of the signal between the potential at the particular electrode placed on the patient's chest and the potential at Wilson's central terminal. Wilson's central terminal refers to the average potential between the RA, LA, and LL electrodes, shown simplified in FIG. 2. The three limb electrodes are connected through equal valued resistors to a common node and the voltage at this node, the Wilson central terminal, is the average of the voltages at each electrode. Each of the leads V1-V6 is compared to Wilson terminal, for example, lead V1 is the signal between electrode V1 and Wilson's central terminal.

It is not always clear when beginning the treatment what type of monitoring will be needed in the future. The patient may go under a preliminary examination and a 3- or 5-lead ECG may be applied. Sometimes further examinations are needed e.g. for eliminating certain illnesses that can be detected by recording 12-lead ECG. Changing from a 5-lead ECG to a 12-lead ECG may be time consuming and difficult. Changing the electrode set and detaching and reattaching the electrodes can take considerable time, particularly if carried out by a non-specialist. This problem could be solved by always using the 12-lead or the 15-lead ECG electrode set and cable and only using the electrodes that are needed for that particular measurement. However, the 12-lead and the 15-lead ECG measurement cables are typically thick and long which makes the nursing staff favor the smaller and more convenient 5-lead ECG measurement electrode set. In order to address this changing need, ECG systems have been developed that include a 5-lead ECG main unit and a 12-lead ECG extension unit that can be configured to operate with the 5-lead main unit. In order to combine these systems, a common mode reference signal must be shared between the systems.

U.S. Pat. No. 7,881,778, which is commonly owned with the present application, discloses a floating patient data acquisition system with an expandable ECG measurement system. The patient side acquisition units form a modular ECG measurement system which comprises a 5-lead ECG main measurement unit that is expandable by a 12-lead ECG extension unit. When the signals acquired by the 5-lead ECG main measurement unit and the 12-lead ECG extension unit are combined, a full 12-lead ECG signal is formed. The '778 patent requires a common Wilson terminal signal or value to be shared among all of the data acquisition units. For example, a 5-lead ECG can be acquired first and in case closer examination is needed, the 5-lead ECG measurements can be expanded merely by applying five additional electrodes provided by the 12-lead ECG extension unit. Since the measurement units use the same common Wilson terminal, the signals may be combined to form a full 12-lead ECG signal. The '778 patent requires that the main measurement unit and the extension unit share the same common ground potential. The common Wilson terminal signal is then referenced to this common ground potential when transmitted from the main measurement unit to the extension unit or units.

As discussed above, in existing patient monitoring devices, the number of electrocardiogram (ECG) electrodes can be chosen by the user by simply applying different number of lead wires into a connector block on the monitor. By this means, the ECG measurement can be reconfigured from 5-lead monitoring to 12-lead monitoring based on the needs of the clinicians.

In the context of body-worn ECG devices, e.g. wireless battery powered sensors or USB powered sensors, a similar modular reconfiguration is most conveniently constructed by adding on, or removing actual measurement electronics, rather than just the lead wires. By this means the device can physically be made smaller and cable connectors can be avoided. To be able to modularly add chest-leads to a main unit containing the limb-leads, a reference signal, such as the Wilson's central terminal or the right arm electrode, is typically shared between the devices. Since body-worn sensors are in contact with the human skin and therefore exposed to sweat and other fluids, reliability concerns are raised when the sweat or other fluids are present around galvanic contacts. Therefore an alternate, more reliable, solution for passing a common mode reference signal or voltage value between the main unit and one or more extension units is needed and desired.

SUMMARY

The present disclosure relates to a data acquisition system for obtaining ECG signals from a patient. More specifically, the present disclosure relates to a data acquisition system that allows for the expansion of an ECG monitoring main unit through the addition of an extension unit.

The data acquisition system of the present disclosure includes a main unit that is connected to a plurality of limb electrodes that are located on the limbs of a patient. The main unit receives a plurality of analog signals from the limb electrodes and is able to generate a first ECG signal based on these analog signals. The first ECG signal can be relayed to a host ECG monitoring system. As an illustrative example, the main unit can be a 5-lead ECG measurement unit.

The data acquisition system further includes an extension unit that can be used in combination with the main unit. The extension unit receives a plurality of analog signals from a plurality of chest electrodes that are located on the patient in a well-known pattern. The extension unit receives the plurality of analog signals from the chest electrodes and generates a second ECG signal. The first and second ECG signals from the main unit and the extension unit, respectively, can be combined to create a 12-lead ECG.

In order for the first and second ECG signals to be combined, a common mode signal connection is formed between the main unit and the extension unit. The common mode signal connection communicates a common mode signal between the main unit and the extension unit. Both the main unit and the extension unit utilize the common mode signal to generate the first and second ECG signals.

In one embodiment of the disclosure, the common mode signal is a common ground that exists between the main unit and the extension unit. The common ground existing between the main unit and the extension unit allows the first and second ECG signals to be generated based upon the same common ground signals. In this case, the common mode reference signal is measured and optionally digitized inside the main unit against the ground potential. This common mode reference signal is then either used in the main unit or transmitted to the host ECG monitoring system for calculating the final electrocardiogram.

In another embodiment of the disclosure, the common mode signal is an analog signal that is provided to both the main unit and the extension unit from one of the limb electrodes, such as the RA electrode. The common analog signal from the limb electrode allows both the main unit and the extension unit to generate the same common mode reference signal without any direct electrical connection required between the main unit and the extension unit. In one embodiment of the disclosure, the common analog signals obtained from a limb electrode, such as the right arm (RA) electrode, is provided to both the main unit and the extension unit along with a shared right leg (RL) electrode for equalizing the potentials of the human body and the measurement electronics.

In another contemplated embodiment, the common mode signal is communicated from the main unit to the extension unit through an optical transmission path. The optical transmission path eliminates the requirement for any wired connection between the main unit and the extension unit. The optical signal from the main unit is derived from a voltage present at one or more of the limb electrodes. In one embodiment, the optical signal is derived from a voltage present at the right arm (RA) electrode of the main unit. Alternatively, the optical signal could be a calculated average of many limb electrodes, such as the Wilson's central terminal. The optical signal is received at the extension unit and converted back to a voltage signal that can then be used as the common mode signal between the main unit and the extension unit. For the optical signal to be meaningful, the main unit and the extension unit must share the electronics ground or some other internal reference potential.

The data acquisition system of the present disclosure can be incorporated into an ECG monitoring device. The ECG monitoring device includes a main monitoring control unit that is configured to receive both the first ECG signal and the second ECG signal and operates to combine the first and second ECG signals to generate a combined ECG output. The first and second ECG signals can be relayed to the main monitoring control unit through a wireless communication technique. Alternatively, the main monitoring control unit could be hard wired to the main unit and the extension unit to receive the first and second ECG signals.

BRIEF DESCRIPTION OF THE DRAWINGS

The drawings illustrate the best mode presently contemplated of carrying out the disclosure. In the drawings.

DETAILED DESCRIPTION

Reference will now be made in detail to the embodiments of the present disclosure, examples of which are illustrated in the accompanying drawings.

Figure 3:
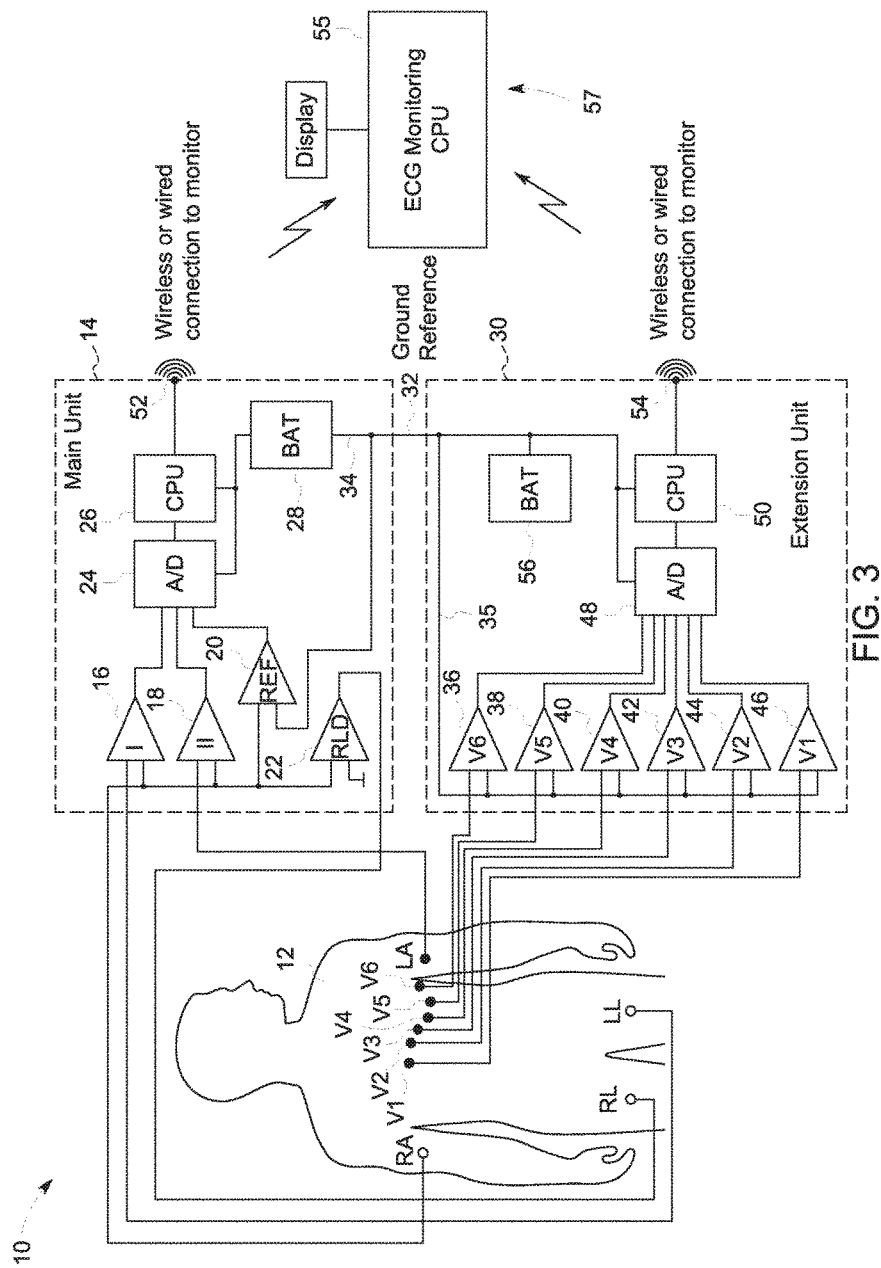
FIG. 3 depicts a data acquisition system according to the present disclosure that is expandable, wherein the main unit and the extension unit share a common mode ground reference.

FIG. 3 illustrates a data acquisition system 10 for obtaining electrocardiogram (ECG) signals from a patient 12. The data acquisition system 10 includes a 5-lead ECG main measurement unit 14 that measures ECG signals from electrodes RA, LA, LL and RL. As is well known, augmented leads aVR, aVL and aVF are calculated by comparing the measured voltage from each of the limb electrodes to a reference voltage. As illustrated in FIG. 3, amplifiers 16, 18, 20 and 22 are used to compare the signals from the various electrodes to a reference signal from the right arm electrode RA and to feed the output signals from each of the amplifiers to an analog/digital converter 24. Amplifier 22 is a right leg drive (RLD) amplifier that utilizes the RL electrode for equalizing the potential of the human body and the measurement electronics. The A/D converter 24 converts the analog signal into a digital ECG signal that is received by the control unit 26. Both the A/D converter and the control unit 26 are powered by an internal battery 28. The battery 28 includes a ground reference terminal 34 that is supplied to the amplifier 20, which measures the ground reference 34 against the RA electrode. This value is provided to the CPU 26 and used in later processing steps as will be discussed below.

Figure 1:
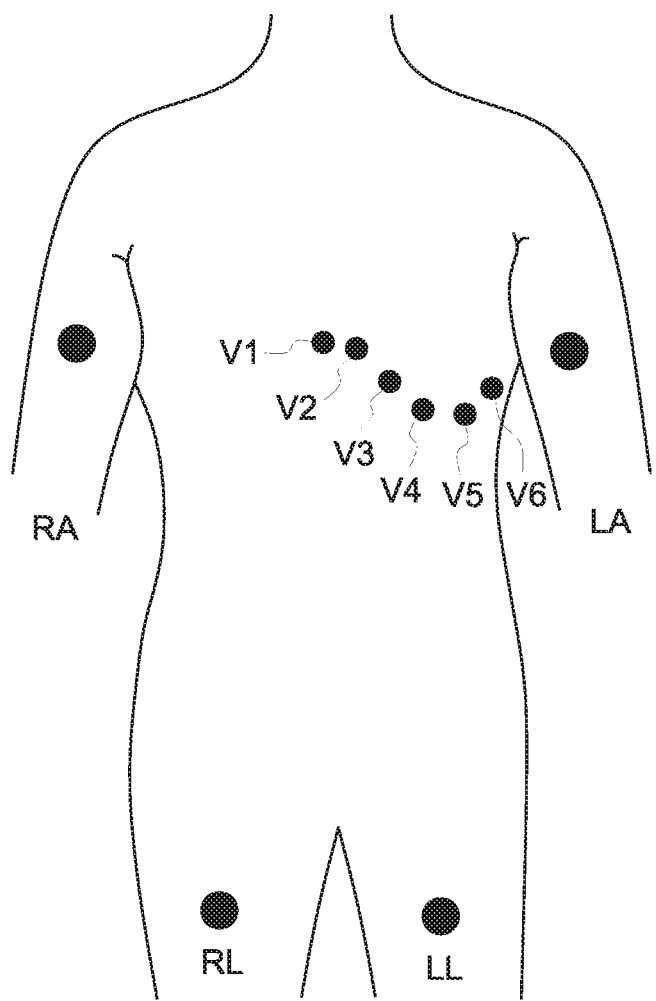
FIG. 1 depicts the standard electrode placement of a 12-lead ECG measurement.
Figure 2:
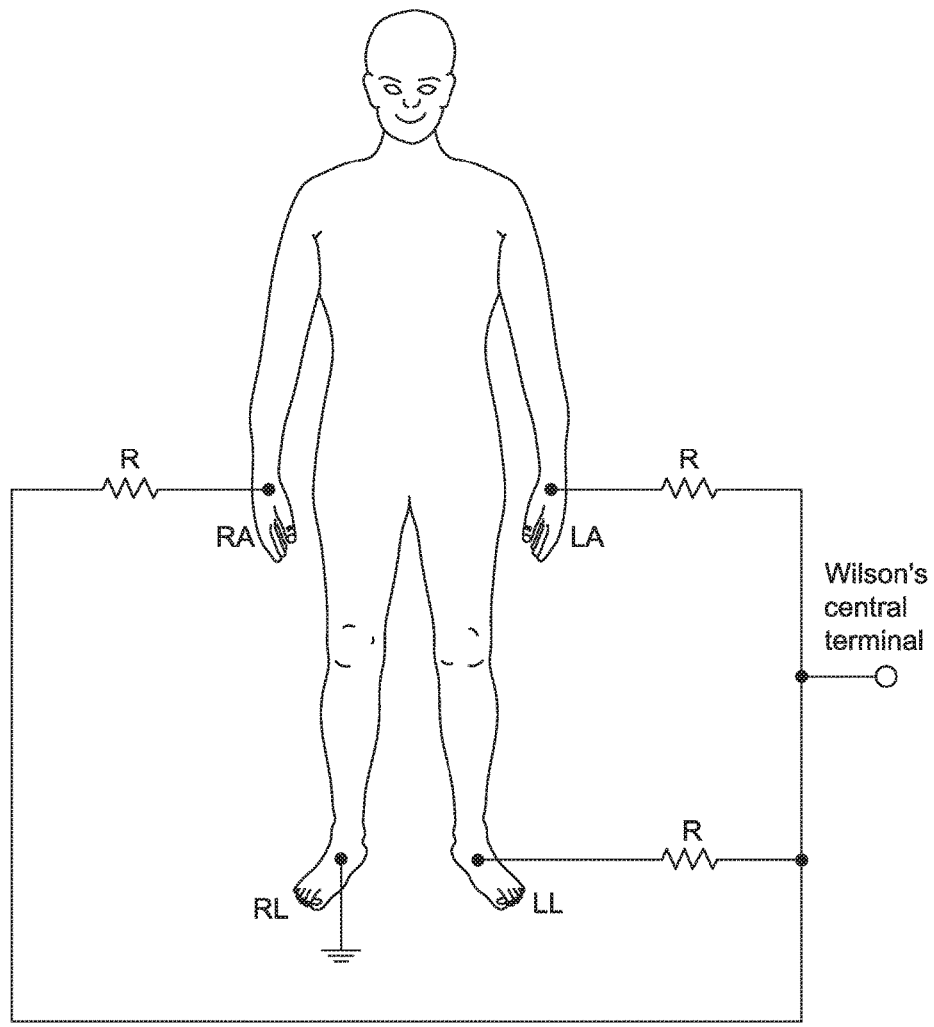
FIG. 2 depicts the connection of electrodes to the body to obtain Wilson's central terminal.

When it is desired to expand the data acquisition system 10, a 12-lead ECG extension unit 30 can be added to the system in order to allow the system to make a 12-lead ECG measurement. When such extension unit 30 is added, the voltage signal from each electrode V1-V6 must be compared to the same reference voltage that is used in the main unit 14 such that the outputs from the main unit 14 and the extension unit 30 can be combined. As discussed previously, in prior art systems, the common potential was determined from the Wilson's central terminal shown and described in FIG. 2.

In accordance with the present disclosure, the inner potential is shared between the main unit 14 and the extension unit 30 through a galvanic reference connection, such as a common ground reference line 32. The ground reference line 32 provides a common mode signal between the two units, which is the inner potential between the main unit 14 and the extension unit 30. In the main unit 14, the inner potential and the ground reference line 32 can be compared to Wilson's central terminal (WCT) through processing in the ECG monitoring CPU 55 of a host monitoring system 57.

In the extension unit 30, the common inner potential is supplied along line 35 and used with each of the amplifiers 36-46 along with the voltage signal from each of the electrodes V1-V6 attached to the patient's chest. The output of each of the amplifiers 36-46 is fed into an A/D converter 48. The A/D converter 48 converts the analog signal from each of the amplifiers 36-46 into a digital signal received by the control unit 50 contained within the extension unit 30.

Both the main unit 14 and the extension unit 30 include a wireless or wired transmitter 52, 54 that are used to transmit the determined first ECG signal from the main unit 14 and the determined second ECG signal from the extension unit 40 for further upstream processing by the ECG monitoring CPU 55 of the host monitoring system 57. The ECG monitoring CPU 55 is part of a larger host ECG monitoring system 57 that utilizes the main unit 14 and the extension unit 30 to obtain signals from the patient. The host ECG monitoring system 57 may include a display, data entry devices or other conventional components. As can be understood in FIG. 3, since the reference signal for each of the chest-leads in the extension unit 30 is the same inner potential as the reference signal for the limb-leads in the main unit 14, the measurement signals from the main unit 14 and the extension unit 30 can be combined in the CPU 55 to create a 12-lead ECG measurement.

In the embodiment shown in FIG. 3, the extension unit 30 includes a separate battery 56 from the battery 28 shown in the main unit 14. However, it is contemplated that the modules 14 and 30 could share a common battery in which case there would be an additional galvanic connection between the main unit 14 and the extension unit 30. In an embodiment, such as shown in FIG. 3, in which both the main unit 14 and the extension unit 30 include their own battery, only the single galvanic connection, shown by reference line 32, would be present between the main unit 14 and the extension unit 30. This single galvanic connection between the modules is a prerequisite for transmitting the reference common mode signal from one module to another such that the two modules would share a common ground reference.

Figure 4:
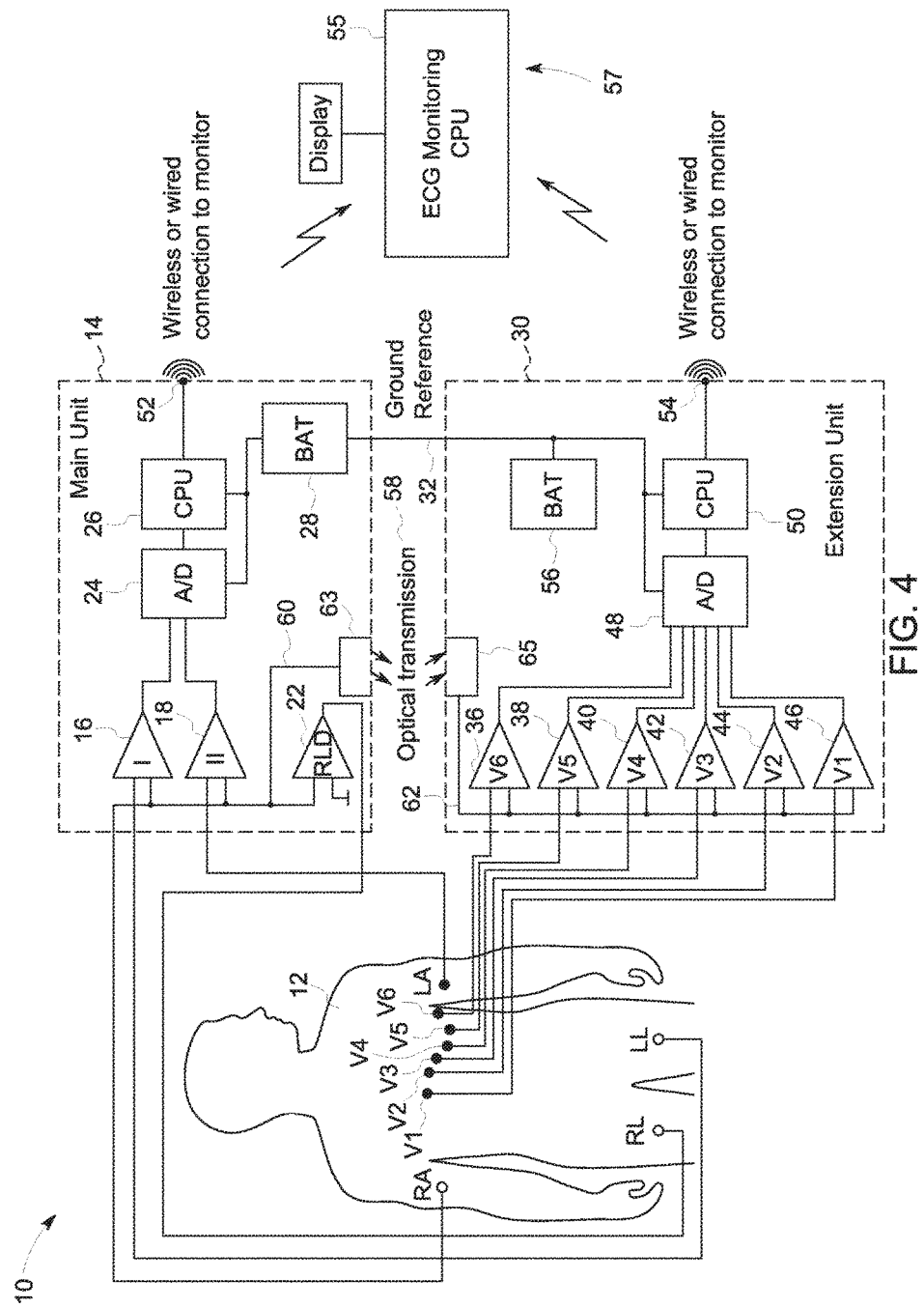
FIG. 4 depicts an alternate embodiment of the data acquisition system in which the main unit and the extension unit include an optical coupling to pass a common mode reference signal between the ECG modules.

FIG. 4 illustrates a second embodiment of a data acquisition system constructed in accordance with the present disclosure. In the drawing figure of FIG. 4, similar reference numerals are utilized for similar components as shown in FIG. 3. Similar to the embodiment of FIG. 3, the ability to add the 12-lead ECG extension unit 30 to the 5-lead main unit 14 requires some type of common mode signal to be shared between the main unit 14 and the extension unit 30 so that the resultant signals from the two units can be combined. In accordance with the embodiment shown in FIG. 4, an optical transmission, as shown by reference numeral 58, is used to share a common mode signal between the main unit 14 and the extension unit 30. In the embodiment shown, a common mode reference signal is present on line 60 and is optically transmitted to the extension unit 30. The extension unit 30 includes a common mode reference signal line 62. This common mode reference line is connected to each of the amplifiers 36-46 and is used as the reference signal for comparing the voltage signals from each of the electrodes V1-V6. The output of each of the amplifiers 36-46 is fed to the A/D converter 38, which converts the analog signals to digital signals presented to the control unit 50 and ultimately transmitted from the wireless transmitter 54.

The optical transmission, shown by reference numeral 58, could be either an analog signal or a digital signal (e.g., a sigma-delta or power modulated signal). The common mode signal transmitted from the main unit 14 to the extension unit 30 would provide a common mode signal that would allow extension from four electrodes to ten electrodes (as shown in FIG. 4) or even beyond to allow a 15- or 16-lead ECG.

In a case in which the optical common mode signal is digitally transmitted, the digitalized signal would be created from the voltage from at least one limb electrode, such as the right arm electrode RA, in an optical conversion circuit 63. In an alternative, preferred embodiment, the digitized signal transmitted to the extension unit 30 would be the Wilson's central terminal, which is calculated in the main unit 14 and transmitted to the extension unit 30. The optical conversion circuit 63 acts to convert the voltage on line 60 into an optical signal that is transmitted by a photodiode by a driving circuit in the conversion circuit 63.

The optical signal from the circuit needs to be reconstructed into its analog equivalent within the extension unit 30. To do this, the extension unit 30 includes a similar optical conversion circuit 65. The circuit 65 includes a photodetector and circuitry that transforms the received optical signal into a voltage. Although the specifics of the optical conversion circuits 63 and 65 are not shown, the specific details of the circuit are a matter of design choice and are contemplated as being within the scope of the present disclosure. As discussed, the optical reference signal is preferably transmitted with light emitting diodes or a laser from the main unit 14 and received by a photodetector, such as a photodiode, contained within the extension unit 30.

In order for the proper transmission of the reference signal utilizing an optical transmission path, the main unit 14 and the extension unit 30 must share the same ground reference. This ground reference is shown in FIG. 4 by reference numeral 32 and is a galvanic connection between the main unit 14 and the extension unit 30. In a contemplated, alternate embodiment, the shared ground reference connection 32 could be eliminated and the RL electrode could be shared between the main unit 14 and the extension unit 30, as shown in the embodiment of FIG. 5.

As with the embodiment shown in FIG. 3, the main unit 14 and the extension unit 30 could share a common battery or, the extension unit 30 could utilize a separate battery 56.

Figure 5:
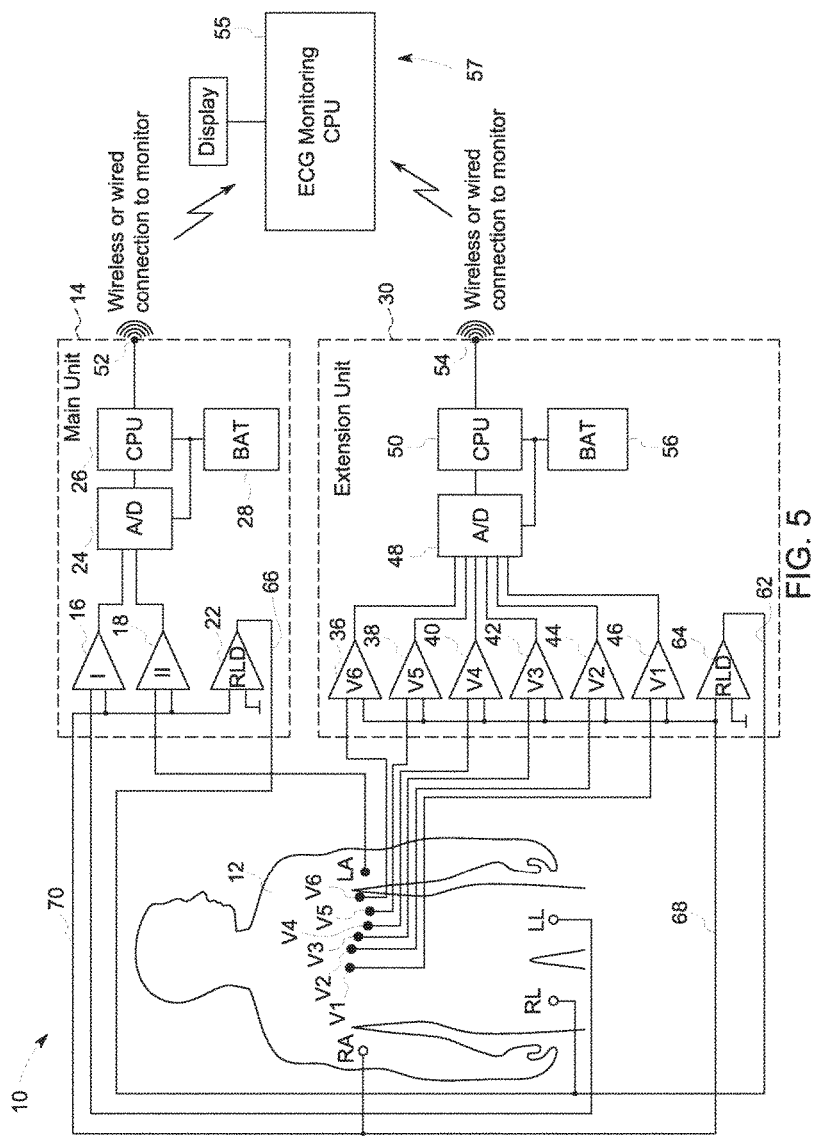
FIG. 5 depicts an alternate configuration of the data acquisition system in which the main unit and the extension unit determine their own common mode reference signal.

FIG. 5 illustrates yet another embodiment of the data acquisition system 10 of the present disclosure. Once again, common reference numerals are utilized throughout FIGS. 3-5 to represent similar components of the data acquisition system. In the embodiment shown in FIG. 5, the expansion of the 5-lead main unit 14 to add the 12-lead extension unit 30 requires some type of common mode reference signal between the main unit 14 and the extension unit 30. In the embodiment illustrated, both the main unit 14 and the extension unit 30 are electrically floating devices that are each capable of determining their own common mode reference signal independently from each other by using the same electrodes on the patient. The wireless ECG units 14 and 30 can be used in parallel with each other and software means can be used to measure either the primary limb-leads or the secondary chest-leads. The chest-leads contained within the extension unit 30 would be referenced to a single limb electrode (preferably to the RA electrode) and this reference electrode would also be used by every extension unit added to the main unit 14 within the system. In addition to this common electrode, both units 14 and 30 need a means for equalizing their potential with the patient's body potential. As illustrated in the embodiment of FIG. 5, both the main unit 14 and the extension unit 30 share the RL electrode. Specifically, the RL electrode is fed by line 62 into the right leg drive (RLD) amplifier 64 and by line 66 to the right leg drive (RLD) amplifier 22 within the main unit 14. The RLD amplifiers 22 and 64 are each also connected to the same common mode reference electrode (e.g. RA electrode in FIG. 5) through lines 68, 70, respectively.

As illustrated in FIG. 5, there is no physical connection between the main unit 14 and the extension unit 30 (neither wired nor wireless) other than the shared limb electrodes, such as but not limited to the RA and RL electrodes. The shared limb electrode between the main unit 14 and the extension unit 30 creates the common mode reference that must be present to combine the measurements from the two units in later processing.

The shared electrode connection shown in FIG. 5 could be implemented by either utilizing a special electrode that includes two cable connectors or with a special electrode clip. Such a special clip in the main unit 14 would include a socket for a shielded plug connector from the extension unit 30. In the embodiment shown in FIG. 5, both the main unit 14 and the extension unit 30 include separate batteries 28, 56 since there is no physical connection between the main unit 14 and the extension unit 30.

Both the main unit 14 and the extension unit 30 can transmit independent signals for further processing through the wireless transmission connections 52, 54. Software means that receive the signal from the main unit 14 and the extension unit 30 can be used to reconfigure the signals to measure either the primary limb-leads or the secondary chest-leads.

Figure 6:
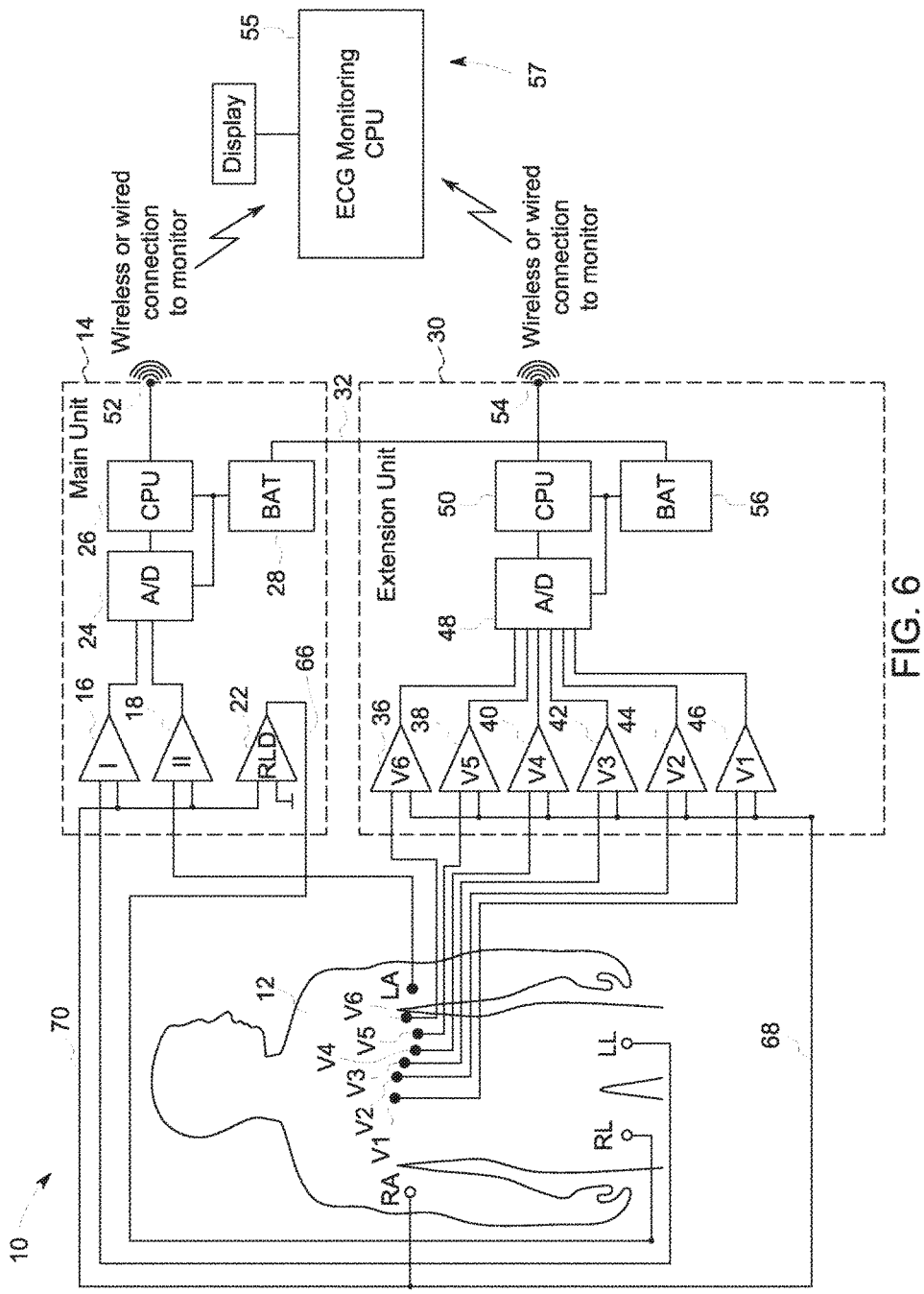
FIG. 6 depicts another alternate configuration of the data acquisition system in which the main unit and the extension unit determine their own common mode reference signal and the units share a common mode ground reference.

In another contemplated embodiment shown in FIG. 6, the main unit 14 and the extension unit 30 share one or more limb electrodes (such as the RA electrode) as in the embodiment of FIG. 5. However, in the alternate embodiment of FIG. 6, the main unit 14 and the extension unit 30 also include a galvanic ground connection 32. The ground connection 32 is not utilized in forming the common mode reference. The common mode reference is solely based on the shared limb electrode voltage, as in FIG. 5.

In the embodiments shown in FIGS. 3-6, the main unit 14 and the extension unit or units 30 are shown communicating directly to the CPU 55 of the host ECG monitoring system 57 using a wireless communication technique. However, it is contemplated that the extension unit 30 could communicate only to the main unit 14 using either wired or wireless communication. In such an embodiment, the main unit 14 would then communicate with the CPU 55 of the host ECG monitoring system 57, which would make the main unit 14 the only link to the host monitoring system 57. The main unit 14, in such an embodiment, would communicate information from both the main unit 14 and the extension unit 30.

As can be understood in the comparisons of FIGS. 3-6, the data acquisition system 10 of the present disclosure allows for the modular expansion of a wireless ECG device by adding an extension unit 30 to a main unit 14. The data acquisition system of the present disclosure provides different opportunities to share a common-mode reference signal or value between the main unit 14 and the extension unit 30 without having to rely upon the Wilson's central terminal or a right arm electrode. The system and method of the present disclosure provides for an alternate, more reliable solution for passing a common known reference signal between the main unit 14 and one or more extension units 30.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system for obtaining a 12-lead electrocardiogram (ECG) from a patient, comprising:
   a plurality of limb electrodes located on the patient;
   a main unit including a first control unit including a first processor configured to receive a plurality of electrophysiological signals from the plurality of limb electrodes and operable to generate a first ECG;
   at least one chest electrode located on the patient;
   at least one extension unit including a second control unit including a second processor configured to receive at least one electrophysiological signal from the at least one chest electrode and operable to generate additional information to the first ECG;
   a single galvanic reference connection between the main unit and the one or more extension units, the single galvanic reference connection providing a common mode reference between the main unit and the extension unit; and
   a host monitoring device including a monitoring processor that received the first ECG signal and the additional information, wherein the common mode reference is used by the first control unit and the second control unit to generate the first ECG and the additional information such that the monitoring processor can combine the first ECG signal and the additional information to generate the 12-lead electrocardiogram from the patient.

2. The system according to claim 1 wherein the common mode reference from the main unit is digitalized and transmitted to the host monitoring device to be combined with additional information from the extension unit to form a part of the electrocardiogram.

3. The system according to claim 2 wherein the common mode reference is digitized and transmitted to the host monitoring devices.

4. The system according to claim 1 wherein the main unit is a 5 electrode ECG measurement unit.

5. The system of claim 1 wherein the single galvanic reference connection between the main unit and the at least one extension unit is a ground potential.

6. The system of claim 1 wherein the common mode reference is derived from at least one analog signal from one or more of the limb electrodes.

7. The system of claim 1 wherein the single galvanic reference connection between the main unit and one or more extension units is an internal reference voltage of the main unit.

8. The system of claim 1 wherein the common mode reference is digitized for subsequent electrocardiogram referencing.

9. The system of claim 1 wherein the single galvanic reference connection between two or more units is established along a lead wire by sharing a measurement electrode.

10. The system of claim 1 wherein the single galvanic reference connection between the main unit and the at least one extension unit is established through adjacent electrodes located on the patient.

11. The system of claim 1 wherein the common mode reference is communicated from the main unit to the at least one extension unit optically.

12. The system of claim 1 wherein the inner potential levels of the main unit and the at least one extension unit are equalized by an interconnection of lead wires.

13. The system of claim 1 wherein the inner potential levels of two or more units are equalized through the patient body by the use of two separate electrodes for this purpose.

14. The system of claim 1 wherein digitalized information from the extension unit is transmitted to the host monitoring device directly.

15. The system of claim 1 wherein digitalized information from the extension unit is transmitted to the host monitoring device through the main unit.

16. The system of claim 1 wherein more than one galvanic connection exists between the main unit and the at least one extension unit, wherein only one of the galvanic connections provides the common mode reference.

* * * * *